US009192589B2

(12) United States Patent
Subramanyam et al.

(10) Patent No.: US 9,192,589 B2
(45) Date of Patent: Nov. 24, 2015

(54) CHALCONES AS ENHANCER OF ANTIMICROBIAL AGENTS

(75) Inventors: Ravi Subramanyam, Mumbai (IN); Laurence Du-Thumm, Princeton, NJ (US); Ghulam Nabi Qazi, New Delhi (IN); Inshad Ali Khan, New Delhi (IN); Krishan Avtar Suri, Jammu (IN); Naresh Kumar Satti, Jammu (IN); Furqan Ali, Jammu Tawi (IN); Nitin Pal Kalia, Jammu Tawi (IN)

(73) Assignees: Colgate-Palmolive Company, New York, NY (US); Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 13/515,836

(22) PCT Filed: Dec. 18, 2009

(86) PCT No.: PCT/US2009/068688
§ 371 (c)(1),
(2), (4) Date: Jun. 14, 2012

(87) PCT Pub. No.: WO2011/075136
PCT Pub. Date: Jun. 23, 2011

(65) Prior Publication Data
US 2012/0251464 A1 Oct. 4, 2012

(51) Int. Cl.
*A61K 36/00* (2006.01)
*A61K 31/122* (2006.01)
*A61K 31/00* (2006.01)
*A61K 31/341* (2006.01)
*A61K 31/40* (2006.01)
*A61K 45/06* (2006.01)
*C07D 207/00* (2006.01)

(52) U.S. Cl.
CPC ............... *A61K 31/122* (2013.01); *A61K 31/00* (2013.01); *A61K 31/341* (2013.01); *A61K 31/40* (2013.01); *A61K 45/06* (2013.01); *C07D 207/00* (2013.01)

(58) Field of Classification Search
CPC ... A61K 31/122; A61K 31/00; A61K 31/341; A61K 31/40; A61K 45/06; C07D 207/00
See application file for complete search history.

(56) References Cited

U.S. PATENT DOCUMENTS

| 5,116,602 | A | 5/1992 | Robinson et al. | |
| 5,683,678 | A | 11/1997 | Heckert et al. | |
| 8,182,843 | B2 * | 5/2012 | Piramal et al. | 424/725 |
| 2003/0138511 | A1 | 7/2003 | Yamamoto et al. | |
| 2004/0147597 | A1 | 7/2004 | Lin et al. | |
| 2006/0078633 | A1 | 4/2006 | Na et al. | |
| 2006/0099237 | A1 | 5/2006 | Modak et al. | |
| 2006/0222601 | A1 | 10/2006 | Sabnis et al. | |
| 2007/0060644 | A1 * | 3/2007 | Vander Jagt et al. | 514/475 |
| 2008/0009528 | A1 | 1/2008 | Blackwell et al. | |
| 2008/0227867 | A1 | 9/2008 | Ley et al. | |

FOREIGN PATENT DOCUMENTS

| EP | 1764363 | 3/2007 |
| JP | 58-213706 A | 12/1983 |
| JP | 1991-122645 | 5/1991 |
| JP | 11-228407 | 8/1999 |
| JP | 2001-512473 | 8/2001 |
| JP | 2003-171274 | 6/2003 |
| JP | 2005-047849 | 2/2005 |
| JP | 2005-298357 A | 10/2005 |
| SU | 677262 | 4/1982 |
| TW | 200637570 | 11/2006 |
| WO | WO 99/66796 | 12/1999 |
| WO | WO 2005/009352 | 2/2005 |
| WO | WO 2005/123023 | 12/2005 |
| WO | WO 2006/105260 | 10/2006 |
| WO | WO 2011/019342 | 2/2011 |
| WO | WO 2011/085098 | 7/2011 |

OTHER PUBLICATIONS

Aas et al., 2005, "Defining the Normal Bacterial Flora of the Oral Cavity", Journal of Clinical Microbiology, 43(11):5721-5732.
Bambeke et al., 2003, "Antibiotic Efflux Pumps in Prokaryotic Cells: Occurance, Impact on Resistance and Strategies for the Future of Antimicrobial Therapy", Journal of Antimicrobial Chemotherapy, 51:1055-1065.
Batovska et al., 2009, "Examination of Growth Inhibitory Properties of Synthetic Chalcones for which Antibacterial Activity was Predicted", European Journal of Medicinal Chemistry, 44(5):2211-2218.
Brehm-Stecher et al., 2003, "Sensitization of *Staphylococcus aureus* and *Escherichia coli* to Antibiotics by the Sesquiterpenoids Nerolidol, Farnesol, Bisabolel and Apritone", Antimicrobial Agents & Chemotherapy, 47(10):3357-3360.
Database GNPD Mintel, 2006, "Oral Spray", XP002616749, Accession No. 590881.
Database GNPD Mintel, 2007, "Toothpaste", XP002616750, Accession No. 702824.
Database GNPD Mintel, 2008, "Toothpaste for Sensitive Teeth", XP002616748, Accession No. 999752.
Hunter-Rinderle et al., 1997, "Evaluation of Cetylpyridinium Chloride Containing Mouthwashes Using in vitro Disk Retention and ex vivo Plaque Glycolysis Methods", Journal of Clinical Dentistry, 8:107-113.
Isaaac et al., 1980, "Chamomile Therapy—Experience and Confirmation", Dtsch. Apoth. Ztg 120:567-570.

(Continued)

*Primary Examiner* — Lezah Roberts
*Assistant Examiner* — Nannette Holloman

(57) ABSTRACT

Compounds are described that are effective in enhancing the efficacy of antimicrobial agents. Also described are methods of using such compounds and compositions that include such compounds. The composition includes a chalcone compound and, optionally, an antimicrobial agent.

10 Claims, No Drawings

(56) References Cited

OTHER PUBLICATIONS

Isaac et al., 1980, "Old and New Methods of Chamomile Therapy", Die Medizinche Welt. 31(31-32):1145-1149, in German.

Kaatz et al., 1997, "Mechanisms of Fluoroquinolone Resistance in Genetically Related Strains of *Staphylococcus aureus*", Antimicrobial Agents & Chemotherapy, 41(12):2733-2737.

Keusch, 2003, "Anthocyanins as pH Indicators & Complexing Agents", http://www.demochem.de/p26_anth-e.html.

Lee et al., 2000, "Interplay Between Efflux Pumps May Provide Either Additive or Multiplicative Effects on Drug Resistance", Journal of Bacteriology, 182(11):3142-3150.

Li et al., 2000, "Interplay Between the MexA-MexB-OprM Multidrug Efflux System and the Outer Membrane Barrier in the Multiple Antibiotic Resistance of Pseudomonas Aeruginosa", Journal of Antimicrobial Chemotherapy, 45:433-436.

Lomovskaya et al., 1999, "Use of a Genetic Approach to Evaluate the Consequences of Inhibition of Efflux Pumps in Pseudomonas Aeruginosa", Antimicrobial Agents & Chemotherapy, 43(6):1340-1346.

Luppold, 1984, "Matricaria Chamomilla—an Old and a New Medicinal Plant", Pharmazie in Unserer Zeit 13(3):65-70.

Moncada et al., 2004, "Tuning the Photochromic Properties of a Flavylium Compound by pH", European Journal of Organic Chemistry, 2004(2):340-312.

Nikaido, 1994, "Prevention of Drug Access to Bacterial Targets: Permeability Barriers and Active Efflux", Science 264:382-388.

PCT/US09/053500—ISR and Written Opinion mailed Feb. 3, 2011.
PCT/US2009/068688—ISR and Written Opinion mailed Oct. 5, 2010.
PCT/US2009/068688—Written Opinion mailed Dec. 5, 2011.
PCT/US2011/020370—ISR and Written Opinion mailed May 7, 2012.

Sato et al., 1992, "Antimicrobial Activity of DU-6859, a New Potent Fluoroquinolone, Against Clinical Isolates", Antimicrobial Agents & Chemotherapy, 36(7):1491-1498.

Shintre et al., 2006, "Efficacy of an Alcohol-Based Healthcare Hand Rub Containing Synergistic Combination of Farnesol and Benzethonium Chloride", International Journal of Hygiene Environmental Health, 209(5):477-487.

Spratt, 1994, "Resistance to Antibiotics Mediated by Target Alterations", Science 264(5157):388-393.

Szalontai et al., 1973, "Further Details on the Bactericidal and Fungicidal Action of Biologically Active Substances of Martricaria chamomillia L", Dtsch. Apoth. Ztg. 115:912.

Szalontai et al., 1975, "Further Details on the Bactericidal and Fungicidal Action of Biologically Active Substances of Martricaria chamomillia L.", Pharmaz. Ztg. 120:982.

Tanaka et al., 1993, "Antimicrobial Activity of DV-7751a, a New Fluoroquinolone", Antimicrobial Agents & Chemotherapy, 37(10):2112-2118.

Urban et al., 1987, Definition of Antibiotics, Roche Lexikon Medizin, 80-81, in German.

Webber et al., 2003, "The Importance of Efflux Pumps in Bacterial Antibiotic Resistance", Journal of Antimicrobial Chemotherapy, 51:(1)9-11.

Yun et al., 2002, "In Vitro and in Vivo Antibacterial Activities of DW286, a New Fluoronaphthyridone Antibiotic", Antimicrobial Agents & Chemotherapy, 46(9):3071-3074.

Indian Drugs, 1987, 24(10):492-493.

Stavri et al., "Bacterial efflux pump inhibitors from natural sources," Journal of Antimicrobial Chemotherapy, 2007, vol. 59, p. 1247-1260.

Alvarez et al., 2008, "Antimicrobial activity and synergism of some substitutes flavonoids," Folia Microbiol. 53(1):23-28.

Sato et al., 2004, "Variation in synergistic activity by flavone and its related compounds on the increased susceptibility of various strains of methicillin-resistant *Staphylococcus aureus* to β-lactam antibiotics," International J. Antimicrobial Agents 24:28-35.

Zhang, 1996, "Pharmacological Effects and Structure-activity Relationship of Chalcones Compounds," Foreign Medical Sciences 23(4):218-223.

\* cited by examiner

US 9,192,589 B2

CHALCONES AS ENHANCER OF ANTIMICROBIAL AGENTS

CROSS-REFERENCE TO RELATED APPLICATIONS

This application is a national stage entry under 35 U.S.C. §371 of International Patent Application No. PCT/US2009/068688, filed 18 Dec. 2009, which is incorporated herein by reference.

FIELD OF THE INVENTION

The invention relates to the field of antimicrobial agents and to compounds capable of enhancing the efficacy of antimicrobial agents. Such enhancers can be used to improve the efficacy of antimicrobial agents in a variety of fields, including for example, improving the efficacy of antimicrobial agents to treat oral conditions brought about by the presence of pathogenic microorganisms (e.g., gingivitis, plaque, etc.). The invention also provides processes for preparation of such compounds, compositions which include such compounds, and the use of the compounds and compositions in methods for treatment of microbial infections and other disorders caused by pathogenic microorganisms.

BACKGROUND OF THE INVENTION

A variety of human ailments owe their origin to pathogenic microorganisms, which include bacteria, virus and fungi. The presence of such pathogenic microorganisms lead to septicaemia, serious infections of upper and lower respiratory tract, CNS, meningitis, intra-abdominal tissue including peritoneum, genito-urinary tract, skin, and soft tissue, and a variety of other infections like systemic mycosis, candidiasis including infections caused by dermatophytes. During last 100 years, significant progress has been made to combat the diseases caused by such a large family of microbes with innumerable therapeutic agents of diverse chemical and biological nature that have become available as a short and long term cure. Such antimicrobials include aminoglycosides, penicillins, cephalosporins, macrolides, glycopeptides, fluoroquinolones, tetracycline, first and second line anti-TB drugs, anti-leprosy, anti-virals, polyene, triazole and imidazole anti-fungals, combinations like pyrimidine derivatives and trimethoprim and sulphamethoxizole.

The constant use of antibiotics in the hospital environment has selected bacterial populations that are resistant to many antibiotics. These populations include opportunistic pathogens that may not be strongly virulent but that are intrinsically resistant to a number of antibiotics. Such bacteria often infect debilitated or immunocompromised patients. The emerging resistant populations also include strains of bacterial species that are well known pathogens, which previously were susceptible to antibiotics. The newly acquired resistance is generally due to DNA mutations, or to resistance plasmids (R plasmids) or resistance-conferring transposons transferred from another organism. Infections by either type of bacterial population, naturally resistant opportunistic pathogens or antibiotic-resistant pathogenic bacteria, are difficult to treat with current antibiotics. New antibiotic molecules which can override the mechanisms of resistance are needed.

Over the years bacteria have developed several different mechanisms to overcome the action of antibiotics. These mechanisms of resistance can be specific for a molecule or a family of antibiotics, or can be non-specific and be involved in resistance to unrelated antibiotics. Specific mechanisms include degradation of the drug, inactivation of the drug by enzymatic modification, and alteration of the drug target (B. G. Spratt, Science 264:388 (1994)). There are, however, more general mechanisms of drug resistance, in which access of the antibiotic to the target is prevented or reduced by decreasing the transport of the antibiotic into the cell or by increasing the efflux of the drug from the cell to the outside medium. Both mechanisms can lower the concentration of drug at the target site and allow bacterial survival in the presence of one or more antibiotics which would otherwise inhibit or kill the bacterial cells. Some bacteria utilize both mechanisms, combining a low permeability of the cell wall (including membranes) with an active efflux of antibiotics. (H. Nikaido, Science 264:382-388 (1994)).

Decreasing the permeability of the outer membrane, by reducing either the number of porins or by reducing the number of a certain porin species, can decrease the susceptibility of a strain to a wide range of antibiotics due to the decreased rate of entry of the antibiotics into the cells. However, for most antibiotics, the half-equilibration times are sufficiently short that the antibiotic could exert its effect unless another mechanism is present. Efflux pumps are an example of such other mechanism. Once in the cytoplasm or periplasm a drug can be transported back to the outer medium. This transport is mediated by efflux pumps, which are constituted of proteins. Different pumps can efflux specifically a drug or group of drugs, such as the NorA system that transports quinolones, or Tet A that transports tetracyclines, or they can efflux a large variety of molecules, such as certain efflux pumps of *Pseudomonas aeruginosa*. In general, efflux pumps have a cytoplasmic component and energy is required to transport molecules out of the cell. Some efflux pumps have a second cytoplasmic membrane protein that extends into the periplasm.

The Multicomponent efflux pumps, belonging mainly to the resistance-modulation-division (RND) family members, found mostly in gram-negative bacteria, include the MDR pumps AcrAB-TolC and MexAB-OprM from *E. coli* and *Pseudomonas aeruginosa*. Interplay between efflux pumps may provide either additive or multiplicative effects on drug resistance (A. Lee et al., J. of Bacteriology, 2000, 182: 3142). MexAB-OprM, MexCD-OprJ, MexEF-OprN, MexXY-OprM, AcrAB-TolC, AcrEF, MarA, SoxS, and/or Tet pump/s are known to be present in Gram negative organisms such as *P. aeruginosa* and *E. coli* and are reviewed in recent publications and papers, such as Webber and Piddock, J. of Antimicrobial Chemother, 2003, 51: 39-11; Bambeke et. al J. of Antimicrobial Chemother, 2003, 51: 1055-1056, 74; Xian Zhi Li et. al., Journal of Antimicrob. Chemother., 2000, 45: 433 436; O Lomovskaya, et. al., Antimicrob. Agents and Chemother., 1999, 43: 1340 1346.

A biofilm is a structured group of microorganisms encapsulated within a self-developed polymeric extracellular matrix. Biofilms are typically adhered to a living or inert surface. In the human or animal body biofilms can form on any internal or external surface. Biofilms have been found to be involved in a wide variety of microbial infections in the body and, therefore, cause a number of conditions including urinary tract infections, middle-ear infections, formation of dental plaque and gingivitis.

Microorganisms present in a biofilm have significantly different properties from free-floating microorganisms of the same species. This is because the polymeric extracellular matrix acts to protect the microorganisms from the surrounding environment allows the microorganisms to cooperate and interact in various ways which are not exhibited by free-floating microorganisms. These complex communities of microorganisms present a unique challenge in that they are often resistant to classical means of antimicrobial control. Bacteria living in a biofilm exhibit increased resistance to antibiotics because the dense extracellular matrix and the outer layer of cells protect the interior of the biofilm from the effects of the antibiotics. Therefore, known antimicrobial agents will not have the same effect on bacteria present in a biofilm.

Thus, cellular factors affecting transport (both active and passive transport) of antibiotics (and antibacterial agents) into bacterial cells are important components of antibiotic resistance for many bacterial species. There exists a need to provide compounds and compositions that enhance the efficacy of antimicrobial agents, even when the efficacy of the antimicrobial may be affected adversely by antibiotic resistance.

SUMMARY OF THE INVENTION

The present invention is aimed to circumvent such problems and use of the products of the present invention offer a low dose regimen that produces enhanced therapeutic action comparable to that of standard dose of a drug alone.

A feature of the invention is to provide pharmaceutical compositions comprising the compounds of the invention. One embodiment includes a composition comprising at least one of the compounds of formula 1-4 and in addition, may also include an antibiotic or antimicrobial compound. Yet another feature of the invention relates to a method of treatment of infections using the compounds of the invention or compositions comprising them. Treatment comprises oral, parenteral administration and/or topical application of an effective amount of the compound of the invention or its compositions, whether single or in combination with an antibiotic or antimicrobial agent or two or more compounds of this invention.

This invention relates the use of synthetic chalcones as enhancers for antimicrobial (and antibacterial) agents. The invention more particularly relates to chalcones and compositions containing chalcones selected from the group consisting of 3-(4"-Hydroxy-3"-methoxy-phenyl)-1-(2'-hydroxy-5'-methoxy-phenyl)-prop-2-ene-1-one (CK-1—formula 2), 3-(4'-Hydroxy-3'-methoxy-phenyl)-1-phenyl-prop-2-ene-1-one (CK-4—formula 1), 3-(2",3"-Dimethoxy-phenyl)-1-furan-2-yl-prop-2-ene-1-one (CK-14—formula 3), 3-(2",5"-dimethoxy-phenyl)-1-(1H-pyrrol-2-yl)-prop-2-ene-1-one (CK-16—formula 4), and mixtures thereof.

DESCRIPTION OF THE PREFERRED EMBODIMENT

It should be understood that the detailed description and specific examples, while indicating embodiments of the invention, are intended for purposes of illustration only and are not intended to limit the scope of the invention.

The following definitions and non-limiting guidelines must be considered in reviewing the description of this invention set forth herein. The headings (such as "Field of the Invention," "Background of the Invention," and "Summary of the Invention,") used herein are intended only for general organization of topics within the disclosure of the invention, and are not intended to limit the disclosure of the invention or any aspect thereof. In particular, subject matter disclosed in the "Background of the Invention" may include aspects of technology within the scope of the invention, and may not constitute a recitation of prior art. Subject matter disclosed in the "Summary of the Invention" is not an exhaustive or complete disclosure of the entire scope of the invention or any embodiments thereof. Classification or discussion of a material within a section of this specification as having a particular utility (e.g., as being an "active" or a "carrier" ingredient) is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Background of the Invention is intended merely to provide a general summary of assertions made by the authors of the references, and does not constitute an admission as to the accuracy of the content of such references.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. In addition, the compositions and the methods may comprise, consist essentially of, or consist of the elements described therein.

As used herein, the word "include," and its variants, is intended to be non-limiting, such that recitation of items in a list is not to the exclusion of other like items that may also be useful in the materials, compositions, devices, and methods of this invention.

As used herein, the term "about," when applied to the value for a parameter of a composition or method of this invention, indicates that the calculation or the measurement of the value allows some slight imprecision without having a substantial effect on the chemical or physical attributes of the composition or method. If, for some reason, the imprecision provided by "about" is not otherwise understood in the art with this ordinary meaning, then "about" as used herein indicates a possible variation of up to 5% in the value.

As referred to herein, all compositional percentages are by weight of the total composition, unless otherwise specified.

The present embodiments include compositions comprising chalcones, 3-(4"-Hydroxy-3"-methoxy-phenyl)-1-(2'-hydroxy-5'-methoxy-phenyl)-prop-2-ene-1-one (CK-1—formula 2), 3-(4'-Hydroxy-3'-methoxy-phenyl)-1-phenyl-prop-2-ene-1-one (CK-4—formula 1), 3-(2",3"-Dimethoxy-phenyl)-1-furan-2-yl-prop-2-ene-1-one (CK-14—formula 3), 3-(2",5"-dimethoxy-phenyl)-1-(1H-pyrrol-2-yl)-prop-2-ene-1-one (CK-16—formula 4), and mixtures thereof. These compounds and compositions are believed to have the properties of enhancing efficacy in vitro screening, when combined with various anti-infective agents using bacteria, viruses and yeast. These compositions and compounds also were efficacious when tested in vivo using mice and guinea pig models infected with microorganisms. The structures of the chalcones of the preferred embodiments are provided in the table below, which illustrates the synthesis of the compounds.

The compounds of the present invention have not been reported as being useful for enhancing the bio efficacy of the drugs, particularly anti-infective drugs such as described in the present invention. The syntheses of the compounds have been accomplished through the combination of various chemical steps known in the art of synthesis. A person having ordinary skill in the art will be capable of synthesizing the compounds described in the embodiments, using the guidelines provided herein.

The chalcone derivatives of formula 2, i.e. 3-(4"-Hydroxy-3"-methoxy-phenyl)-1-(2'-hydroxy-5'-methoxy-phenyl)-prop-2-ene-1-one and 1 i.e. 3-(4'-Hydroxy-3'-methoxy-phenyl)-1-phenyl-prop-2-ene-1-one were synthesised by the condensation of acetophenone derivatives with substituted aromatic aldehydes in alkaline or acidic conditions, whereas in the case of compounds 3 and 4 the condensation was between substituted aromatic aldehyde and 2-acetylfuran and substituted aromatic aldehydes and and 2-acetylpyrrole respectively. The synthesis and structure of formula 1-4 are shown in the schematic below.

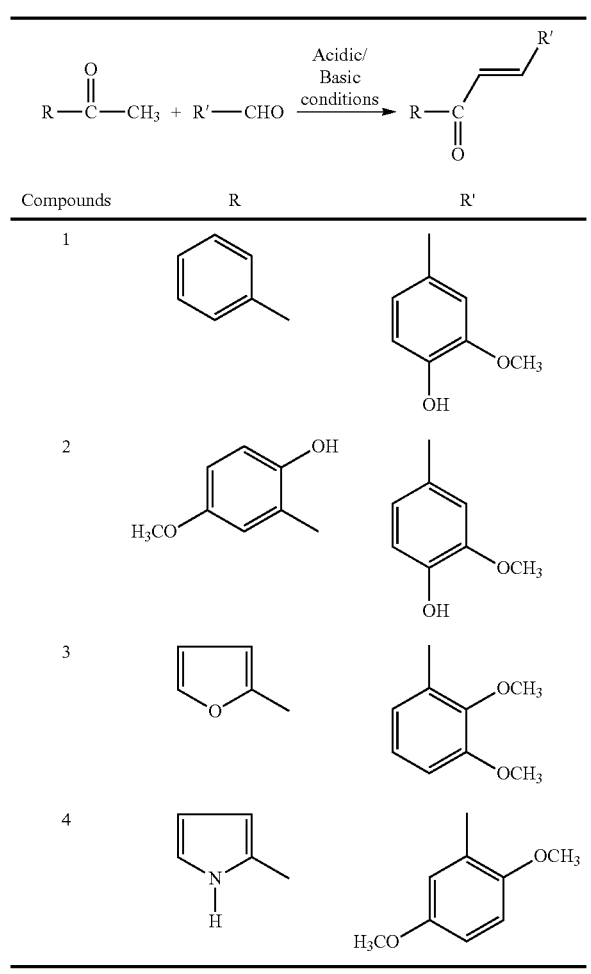

Synthesis of Chalcone 1 to 4

As an illustrative example, the chemical structure of compound 1, 3-(4'-Hydroxy-3'-methoxy-phenyl)-1-phenyl-prop-2-ene-1-one, also named phenyl-3-methoxy-4-hydroxystyryl ketone, is as follows:

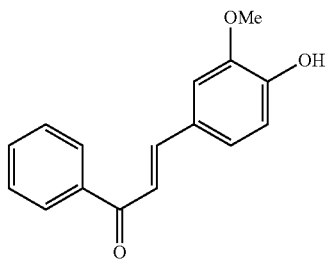 [SMILES: COc1cc(/C=C/C(=O)c2ccccc2)ccc1O]

While not intending on being limited to any theory or mode of operation, these compounds are believed to inhibit cellular efflux pumps of bacteria or other microbes. Such efflux pumps export substrate molecules from the cytoplasm in an energy-dependent manner, and the exported substrate molecules can include antibacterial agents or other antimicrobial agents and disinfectants. Such efflux pump inhibitors are useful, for example, for treating microbial infections by reducing the export of a co-administered antimicrobial agent or by preventing the export of a compound synthesized by microbes (e.g., bacteria) to allow or improve their growth. An example of reducing the export of such a compound is inhibiting iron availability for the microbe by reducing the export of siderophores. While not intending on being bound by any theory of operation, the compounds of the invention also may enhance the efficacy of certain antibacterial agents by inhibiting biofilm formation and/or degrading a biofilm. The compounds and compositions therefore are believed to be useful in preventing conditions caused by biofilm formation. Thus, this invention also provides compositions which include such compounds and methods for treating microbial infections, conditions caused by the presence of pathogenic microorganisms, and conditions caused by biofilm formation.

It is therefore a feature of the invention to provide a method of suppressing growth of a bacterium or a fungus, comprising contacting said bacterium or fungus with a chalcone compound of the invention in the presence of a concentration of antibacterial or antifungal agent below the minimum inhibitory concentration (MIC) of said bacterium or fungus.

It is an additional feature of the invention to provide methods for treating the infections in humans and animals, caused by sensitive and resistant microbial strains using an antimicrobial agent and a chalcone compound of the invention in an amount sufficient to reduce antibiotic resistance, or an amount sufficient to inhibit biofilm formation and/or degrading a biofilm, wherein the chalcone compound increases the susceptibility of the microbe to the antimicrobial agent.

Another feature of the invention provides a method for prophylactic treatment of a human or animal, comprising administering to said human or animal at risk of a microbial infection a chalcone compound of the invention, wherein the compound decreases the pathogenicity of a microbe in the human or animal.

Another feature of the invention provides a method for prophylactic treatment of human or animal, comprising administering to said human or animal at risk of a microbial infection an antimicrobial agent and a chalcone compound of the invention, wherein the compound increases the susceptibility of a microbe to the antimicrobial agent.

Another feature of the invention provides a method of treatment using a chalcone compound of the invention by administering, systemically or topically, the compound to the affected human or animal, thereby avoiding the toxic effects associated with mixtures of the compounds of the invention.

Another feature of the invention is to enhance the antimicrobial activity of an antimicrobial agent against a microbe by contacting the microbe with an antimicrobial agent and a chalcone compound of the invention.

The term "drug" used in this disclosure refers to a chemical entity capable of affecting organism's patho-physiology, and can be used for the treatment or prevention of disease. Drugs include a number of classes of compounds, including, but not limited to, aminoglycoside, penicillins, cephalosporins and other β-lactam agents, macrolides, glycopeptides, fluoroquinolones, tetracyclines, first and second line anti-TB drugs, anti-leprosy, antivirals, polyene, triazole, and imidazoles and combinations like pyrimidines, sulphamethoxazole, phenolic compounds such as triclosan, magnolol and their derivatives, honokiol and their derivatives, quaternary ammonium compounds such as cetylpyridinium chloride. Drugs may be a pro-drug, activated or metabolised form, consisting of charged, uncharged, hydrophilic, hydrophobic or zwitter-ion species which make their entry by simple diffusion, carrier mediated transport dependent and not dependent on energy requirements, through ion and/or voltage gated channels.

The particularly preferred chalcone derivatives of formula 1-4 were selected from the following set of compounds prepared by the methods described in the examples. One or more of the chalcone derivatives can be used in the embodiments described herein.

1. 3-(4'-Hydroxy-3'-methoxy-phenyl)-1-phenyl-prop-2-ene-1-one
2. 3-(4"-Hydroxy-3"-methoxy-phenyl)-1-(2'-hydroxy-5'-methoxy-phenyl)-prop-2-ene-1-one,
3. 3-(2",3"-Dimethoxy-phenyl)-1-furan-2-yl-prop-2-ene-1-one
4. 3-(2",5"-dimethoxy-phenyl)-1-(1H-pyrrol-2-yl)-prop-2-ene-1-one
5. 1-(2-Furyl)-3-(3,4,dimethyoxyphenyl)prop-2-en-1-one
6. 1-(2-Furyl)-3-phenylprop-2-en-1-one
7. 1-(2-Furyl)-3-(3,4,5-methylenedioxy phenyl)prop-2-en-1-one
8. 1-(2-Furyl)-3-(3-hydroxy,-methyoxyphenyl)prop-2-en-1-one
9. 1-(2-Furyl)-3-(3-nitrophenyl)prop-2-en-1-one
10. 1-(2-Furyl)-3-(3,hydroxyphenyl)prop-2-en-1-one
11. 1-(2-Furyl)-3-(4,5-nitrophenyl)prop-2-en-1-one
12. 1-(2-Furyl)-3-(3,6-dichlorophenyl)prop-2-en-1-one
13. 1-(2-Furyl)-3-(2,3-dimethyoxyphenyl)prop-2-en-1-one
14. 1-(2-Furyl)-3-(2,5-dimethyoxyphenyl)prop-2-en-1-one
15. 3-(4-nitrophenyl)-1-(1H-pyrrol-2-yl)-propenone
16. 3-(3-nitrophenyl)-1-(1H-pyrrol-2-yl)-propenone
17. 3-(2,5-dichlorophenyl)-1-(1H-pyrrol-2-yl)-propenone
18. 3-(2,3-dimethyoxyphenyl)-1-(1H-pyrrol-2-yl)-propenone
19. 3-(2,3-dicholoro-phenyl)-1-(1H-pyrrol-2-yl)-propenone
20. 3-(2,6-dichlorophenyl)-1-(1H-pyrrol-2-yl)-propenone Particularly appropriate examples of a microbe appropriate for the use with a chalcone compound of the preferred embodiments are pathogenic bacterial species, such as *Streptococcus pneumoniae, Streptococcus pyogenes, Pseudomonas aeruginosa, Escherischia coli, Staphylococcus aureus, Streptococcus mutans, Actinomycetes viscosus, Fusobacterium nucleatum, Porphyromonas gingivalis* which can be intrinsically resistant to commonly used antibacterial agents. It is believed that exposing these bacteria to a chalcone compound of the invention can significantly slow the export of an antibacterial agent from the interior of the cell or the export of siderophores. For instance, overexpression of the norA multidrug transporter has been reported for strains of *S. aureus* for fluoroquinolone resistance both in-vitro (Kaatz and Seo, Antimicrobial agents and Chemother., 1997, 41: 2733-2737). Therefore, if another antibacterial agent is administered in conjunction with the chalcone compound of the invention, the antibacterial agent, which would otherwise be maintained at a very low intracellular concentration by the export process, can accumulate to a concentration that will inhibit the growth of the bacterial cells. This growth inhibition can be due to either bacteriostatic or bactericidal activity, depending on the specific antibacterial agent used. While *P. aeruginosa* is an example of an appropriate bacterium, other bacterial and microbial species including those described above may contain similar broad substrate pumps, which actively export a variety of antimicrobial agents, and thus can also be appropriate targets.

Therefore, illustrating the utility of the chalcone compounds of the invention, inhibiting the efflux pump of *Streptococcus pneumoniae, Streptococcus pyogenes, Pseudomonas aeruginosa, Escherischia coli, Staphylococcus aureus, Streptococcus mutans, Actinomycetes viscosus, Fusobacterium nucleatum, Porphyromonas gingivalis* is believed to permit obtaining one or more of the following biological effects: 1 *Streptococcus pneumoniae, Streptococcus pyogenes, Pseudomonas aeruginosa, Escherischia coli, Staphylococcus aureus, Streptococcus mutans, Actinomycetes viscosus, Fusobacterium nucleatum, Porphyromonas gingivalis* strains will become susceptible to antibiotics that could not be used for treatment of the respective bacterial infections, or become more susceptible to antibiotics which do inhibit the respective bacterial growth; 2 *Streptococcus pneumoniae, Streptococcus pyogenes, Pseudomonas aeruginosa, Escherischia coli, Staphylococcus aureus, Streptococcus mutans, Actinomycetes viscosus, Fusobacterium nucleatum, Porphyromonas gingivalis* strains will become more susceptible to antibiotics currently used for treatment of the respective bacterial infections; 3 virulence of *Streptococcus pneumoniae, Streptococcus pyogenes, Pseudomonas aeruginosa, Escherischia coli, Staphylococcus aureus, Streptococcus mutans, Actinomycetes viscosus, Fusobacterium nucleatum, Porphyromonas gingivalis* will be attenuated because the availability of an essential siderephore bearing element will be hampered; and 4 the inhibition of the pumps or of one of the components of the pumps may be lethal or prevent growth.

Obtaining even one of these effects provides a potential therapeutic treatment for infections by these bacteria. Some or all of the above effects also can be obtained with those microbes, and they are therefore also appropriate targets for detecting or using efflux pump inhibitors. Thus, the term "microbes" include, for example, bacteria, fungi, yeasts, and protozoa.

As indicated, the bacterium to be inhibited through the use of a chalcone compound of the invention can be from other bacterial groups or species, such bacterial groups of species including but not limited to one of the following: *Pseudomonas aeruginosa, Pseudomonas fluorescens, Pseudomonas acidovorans, Pseudomonas alcaligenes, Pseudomonas putida, Stenotrophomonas maltophilia, Burkholderia capacia, Aeromonas hydrophilia, Escherichia coli, Citrobacter freundil, Salmonella tryphimurium, Salmonella typhi, Salmonella paratyphi, Salmonella enteritidis, Shigella dysenteriae, Shigella flexneri, Shigella sonnet, Enterobacter cloacae, Enterobacter aerogenes, Klebsiella pneumoniae, Klebsiella oxytoca, Serratia, marcescens, Francisella tularensis, Morganella morganii, Proteus mirabilis, Proteus vulgaris, Providencia alcalifaciens, Providencia rettgeri, Providencia stu-* artii, *Porphyrompnas gingivalis, Prevotella intermedia, Acinetobacter calcoaceticus, Acinetobacter haemolyticus, Actinomycetes viscosus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus duicreyi, Haemopuilus actinomycetemcomitans, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Morazella, Gardenerella vaginalis, Bacteroides fragilis, Bacteroides distasonis, Bacteroides* 3452A homology group, *Bacteroides distasonis, Bacteroides ovalus, Bacteroides thetaiotaomicron, Bacteroides uniformis, Bacteroides eggerthii, Bacteroides splanchnicus, Clostridium diffile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus mutans, Streptococcus sanguis, Streptococcus salivarius, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. hyicus, *Staphylococcus haemolyticus, Staphylococcus hominis* and *Staphylococcus saccharolyticus*.

The term "efflux pump" refers to a transmembrane protein assembly which exports substrate molecules from the cytoplasm or periplasm of a cell, in an energy dependent fashion. Thus an efflux pump will typically be located in the cytoplasmic membrane of the cell (spanning the cytoplasmic membrane). In Gram-negative bacteria the pump may span the periplasmic space and there may also be portion of the efflux pump which spans the outer membrane.

An "efflux pump inhibitor" is a compound that specifically interferes with the ability of an efflux pump to export its normal substrate, or other compounds such as an antibiotic. The inhibitor may have intrinsic antimicrobial (e.g., antibacterial) activity of its own, but at least a significant portion of the relevant activity is due to the efflux pump inhibiting activity. Of particular interest in the embodiments, are compounds that inhibit the export or activity of efflux pumps which have a broad substrate range which includes antibacterial agents.

In another aspect, this invention provides a method for treating a microbial infection, e.g., a bacterial infection, in an animal by administering to an animal suffering from such an infection one or more chalcone compounds as described above in an amount sufficient to reduce efflux pump activity, or in an amount sufficient to inhibit biofilm formation and/or degrade the biofilm.

In a preferred embodiment, the chalcone compound is one that decreases the pathogenicity of the microbe. Such a decrease in pathogenicity can be obtained, for example, by interfering with essential bacterial element acquisition by inhibiting the transport of siderophores, or by inhibiting or degrading biofilm formation. The pathogenicity may also be reduced by reducing or eliminating the microbial products which cause tissue-damaging effects to the host. Other methods of reducing pathogenicity are, however, also within this aspect.

In certain preferred embodiments, the microbial infection or disorder may be due to bacteria, which may, for example, be any of the bacterial species indicated above, but specifically including *Streptococcus pneumoniae, Pseudomonas aeruginosa, Escherischia coli, Staphylococcus aureus*. Such disorders, when present in the oral cavity include, for example, gingivitis, tooth decay, plaque formation, and the like.

In a related aspect, this invention provides a method of treating an animal suffering from a microbial infection by administering to the animal a chalcone compound of the invention in an amount sufficient to enhance the activity of the antimicrobial agent administered together with the chalcone compound. In this aspect, the chalcone compound may be one that reduces the in vivo viability of a microbe involved in the infection. By reducing the in vivo viability, the infected animal can more readily clear its body of the infection, or the microbes may even be killed. In particular embodiments the animal is a mammal. Also in particular embodiments, the microbe may be from one of a variety of pathogenic bacterial species, specifically including those listed above.

In a related aspect, the invention provides a method for treating a microbial infection in an animal, specifically including in a mammal, by treating an animal suffering from such an infection with an antimicrobial agent and a chalcone compound of the invention that which increases the susceptibility of the microbe for that antimicrobial agent. In this way a microbe involved in the infection can be treated using the antimicrobial agent in smaller quantities, or can be treated with an antimicrobial agent which is not therapeutically effective when used in the absence of the chalcone compound. Thus, this method of treatment is especially appropriate for the treatment of infections using an antimicrobial agent alone due to a need for high dosage levels (which can cause undesirable side effects), or due to lack of any clinically effective antimicrobial agents. However, it is also appropriate for treating infections involving microbes which are susceptible to particular antimicrobial agents as a way to reduce the dosage of those particular agents. This can reduce the risk of side effects, but can also reduce the selection effect for highly resistant microbes resulting from the consistent high level use of a particular antimicrobial agent. In particular embodiment the microbe is a bacterium, which may, for example, be from any of the groups or species indicated above. Also in particular embodiments various antibacterial agents can be used. These include quinolones, tetracyclines, glycopeptides, aminoglycosides, beta-lactams, rifamycins, coumermycins, macrolides, and chloramphenicol.

In particular embodiments an antibiotic of the above classes can be, for example, one of the following:

Beta-Lactam Antibiotics

Imipenem, meropenem, saneftrinem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriazone, cefurozime, cefuzonam, cephaaceterile, cephalexin, cephaloglycin, cephaloridine, cephalothin, cephapirin, cephradine, cefmetazole, cefoxitin, cefotetan, azthreonam, carumonam, flomoxef, moxalactam, amidinocillin, amoxicillin, amiclllin, azlocillin, carbenicillin, benzylpenicillin, carfecillin, cloxacillin, dicloxacillin, methiciloin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, Cefozopran, ME1228, KP-736, CP-6232, Ro 09-1227, OPC-20000, LY206763, Macrolides, azithromycin, clarithromycin, erythromycin, oleandomycin, rokitamycin, rosaramicin, roxithromycin, troleandomycin, telithromycin and other ketolides. Quinolones Amifloxacin, cinoxacin, ciprofloxacin, enoxacin, fleroxacin, flumequine, loMefloxacin, nalidixic acid, norfloxacin, ofloxacin, levofloxacin, oxolinic acid, pefloxacin, difloxacin, marbofloxacin, rosoxacin, temafloxacin, tosufloxacin, sparfloxacin, clinafloxacin, trovafloxacin, alatrofloxacin, grepafloxacin, moxifloxacin, gatifloxacin, gemifloxacin, nadifloxacin, PD131628, PD140248, Q-35, AM-1155, NM394, T-3761, rufloxacin, OPC-17116, DU-6859a (identified in Sato, K. et. al., 1992, Antimicrob Agents Chemnother. 37:1491 98), DV-7751a (identified in Tanaka, M. et. al., 1992 Antimicrob Agents Chemother 37:2212 18).

Tetracyclines

Chlortetracycline, demeclocyline, doxycycline, lymecycline, methacycline, minocycline, oxytetracycline, tetracycline, Aminoglycosides, Amikacin, arbekacin, butirosin, dibekacin, fortimicins, gentamicin, kanamycin, netilmicin, ribostanycin, sisomicin, spectinomycin, streptomycin, tobramycin, clindamycin, lincomycin.

Oxazolidinones

Linezolid, Eperezolid.

Each of the above compounds has been reported in the literature. Other antibiotic compounds that may be identified also can be utilized with the chalcone compounds of this invention.

In the context of the response of a microbe, such as a bacterium, to an antimicrobial agent, the term "susceptibility" refers to the sensitivity of the microbe for the presence of the antimicrobial agent. So, to increase the susceptibility means that the microbe will be inhibited by a lower concentration of the antimicrobial agent in the medium surrounding the microbial cells. This is equivalent to saying that the microbe is more sensitive to the antimicrobial agent. In most cases the minimum inhibitory concentration (MIC) of that antimicrobial agent will have been reduced.

This invention also features a method of enhancing the antimicrobial activity of an antimicrobial agent against a microbe, in which such a microbe is contacted with a chalcone compound of the invention, e.g., a non-tetracycline-specific chalcone compound, and an antibacterial agent. Thus, this method makes an antimicrobial agent more effective against a cell that expresses an efflux pump, or against a cell involved in biofilm formation, when the cell is treated with the combination of an antimicrobial agent and chalcone compound. In particular embodiments the microbe is a bacterium or a fungus, such as any of those described above; the antibacterial agent can be selected from a number of structural classes of antibiotics including, e.g., beta-lactams, glycopeptides, aminoglycosides, quinolones, tetracyclines, rifamycins, coumermycins, macrolides, and chloramphenicol. In particular embodiments an antibiotic of the above classes can be as stated above.

In a further aspect this invention provides pharmaceutical compositions effective for treatment of an infection of an animal, e.g., a mammal, by a microbe, such as a bacterium or a fungus. The composition includes a pharmaceutically acceptable carrier and a chalcone compound as described above. In preferred embodiments, such compositions contain chalcone compounds that are themselves effective antimicrobial agents, even in the absence of another antimicrobial agent (i.e., have intrinsic antimicrobial activity). Thus, pharmaceutical composition including such chalcone compounds can be used either alone or in conjunction with another antimicrobial agent.

Also in preferred embodiments, the chalcone compounds in pharmaceutical compositions of this aspect enhance the effectiveness of an antimicrobial agent, so such compositions would generally be used in combination with such other antimicrobial agent. The invention also provides pharmaceutical compositions similarly effective for treatment of an infection of a mammal, in which the compositions include a chalcone compound and an antimicrobial agent. Similarly, the invention provides antimicrobial formulations that include an antimicrobial agent, a chalcone compound of the invention, and a carrier. In preferred embodiments, the antimicrobial agent is an antibacterial agent.

A "carrier" or "excipient" is a compound or material used to facilitate administration of the compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil, peanut and sesame oils. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8.sup.th Ed., Pergamon Press.

In further aspect, the invention provides a method of making a pharmaceutical composition comprising identifying a chalcone compound of the type described in the above table of formula 1-4; synthesizing the compound, and preparing a pharmaceutical composition containing the compound. The chalcone compound may have the chemical structure as described above. The pharmaceutical composition may also contain one or more antimicrobial agents, e.g., as identified above, and one or more carriers, diluents, and excipients. Further, in preferred embodiments, the chalcone compound is active against a microbe, e.g., a bacterium, as identified above.

Identification of Chalcone Compounds

Identification of chalcone compounds having structures as described for the present invention was performed using screening methods known to those skilled in the art of biological techniques and are described in detail below. However, other screening methods for detecting efflux pump inhibitors can also be used. The inventors have screened a library of synthetic chemicals and identified several compounds that effectively inhibit the respective efflux pumps of *Staphylococcus aureus* 1199B (NorA overexpressing), *Staphylococcus aureus* SA-K2192 (TetK overexpressing), and *Staphylococcus aureus* SA-K2191 (MsrA overexpressing).

The Checkerboard Method:

The checkerboard method is the most frequently used method to access the antimicrobial combinations in vitro. The term "checkerboard" refers to the pattern (of tubes or microtiter plate wells) formed by multiple dilutions of two drugs being tested (Eliopoulos G M, Moellering R C. Antimicrobial Combinations, in: Antibiotics in Laboratory Medicine: USA: Williams & Wilkins). In the present study the checkerboard consisted of columns in which each tube (or well) contains the same amount of the standard drug (antibacterial/antifungal/anti-TB/antiviral) being diluted along the x-axis and rows in which each tube (or well) contains the same amount of the potentiator being diluted on the y-axis. As a result each square in the checkerboard (which represents one tube/well or plate) contained a unique combination of the standard drug and potentiator. The concentration range of standard drug in the present study was 64 µg/ml to 0.03 µg/ml, whereas the potentiator was tested in the range of 500 µg/ml to 0.2 µg/ml. This checkerboard technique can be performed with liquid or semisolid (agar) media.

Agar Method:

In the agar method the agar (Mueller Hinton agar, Middlebrook 7H10 agar) was autoclaved and allowed to cool to 55° C. to 50° C. The combination of the standard drug and the potentiator was added to the agar. Serial two fold dilutions of each of standard drug and the potentiator were prepared in appropriate solvents. In order to maintain the desired concentrations of both agar and drugs, and to rule out the effect of solvent, the volume of solvent (containing standard drug or potentiator) added to agar was kept small (i.e. ≤5% of the total volume). After the agar plates have been poured and allowed to dry, the bacteria to be tested were applied to the surface of agar with a replicating device designed to deliver a standard inoculum (approx $10^4$ cfu/spot). The plates were incubated at 37° C. for 24 hrs (3 weeks in case of *Mycobacterium tuberculosis*).

Broth Method:

The above-mentioned checkerboard was also performed with liquid media in a microtiter plate format. This method was used to study the combination of antibacterial/antifungal/antiviral drugs with potentiator.

Screening of Chalcone Compounds—In-vivo

Inhibitors of the bacterial efflux pumps are generally initially characterised in vitro. Those which show effective inhibition of the pump(s) and which show synergistic activity with antibiotics are selected for evaluation in vivo. Efficacy testing will be done using standard procedures. Primary efficacy evaluation may be done using the murine septicemia model (Yun et al. Journal of Antimicrob. Chemother., 2002, 46: 3071-3074). In this model a supra-lethal dose of bacteria is used to challenge the rodents. Treatment is initiated, varying either or both time(s) of treatment and dose of antibiotic. In these experiments both the antibiotic and the efflux pump inhibitor doses are varied. A positive result is indicated by significant increase in protection from the lethal infection by the combination of the potentiator (the efflux pump inhibitor) and the antibiotic versus the antibiotic alone.

Pharmaceutical Compositions and Modes of Administration

The particular compound identified above can be administered to a patient either by itself, or in combination with an antimicrobial, e.g., antibacterial, agent, or in pharmaceutical compositions where it is mixed with a suitable carrier(s) or excipient(s) or diluent(s). A combination of a chalcone compound with an antimicrobial agent can be of at least two different types. In one, a quantity of a chalcone compound is combined with a quantity of an antimicrobial agent in a mixture, e.g., in a solution or powder mixture. In such mixtures, the relative quantities of the chalcone compound and the antimicrobial agent may be varied as appropriate for the specific combination and expected treatment. In a second type of combination a chalcone compound and an antimicrobial agent can be covalently linked in such manner that the linked molecules can be cleaved within the cell. However, the term "in combination" can also refer to other possibilities, including serial administration of a chalcone compound and other antimicrobial agent. In addition, a chalcone compound and/or another antimicrobial agent may be administered in pro-drug forms, i.e. the compound is administered in a form which is modified within the cell to produce the functional form. In treating a patient exhibiting a disorder of interest, a therapeutically effective amount of an agent or agents such as these is administered. A therapeutically effective dose refers to that amount of the compound(s) that results in amelioration of symptoms or a prolongation of survival in a patient, and may include elimination of a microbial infection.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage and dosage form employed and the route of administration utilized. It is preferable that the therapeutic serum concentration of a chalcone compound should be in the range of 0.1 to 100 mcg/mL.

In the case of dentifrice or oral care compositions, the compounds described herein can be administered with a suitable antibacterial agent, anti-plaque agent, anti-calculus agent, anti-tartar agent, and other oral care actives, as well as combinations of these actives. The compositions may be in the form of a toothpaste, tooth powder, gel, rinse, lozenge, chewing gum, film, and the like. Any suitable antibacterial agent can be used, including natural antibacterial agents, synthetic agents, and the like. The dentifrice compositions typically contain an antibacterial agent, a chalcone compound, an abrasive, a humectant, and an orally acceptable carrier. The respective amounts of the components may vary, and persons having ordinary skill in the art are capable of formulating suitable dentifrice compositions using the guidelines provided herein.

The antimicrobial agent in the composition according to the present invention is not particularly limited, and may be selected from halogenated diphenyl ether (triclosan), herbal extracts or essential oils (e.g., rosemary extract, thymol, menthol, eucalyptol, methyl salicylate), bisguanide antiseptics (e.g., chlorhexidine, alexidine, or octenidine), phenolic antiseptics, hexetidine, povidone iodine, delmopinol, salifluor, metal ions and their salts (e.g., zinc chloride, zinc lactate, zinc citrate, zinc oxide, stannous fluoride, and stannous chloride), sanguinarine, propolis, oxygenating agents (e.g., hydrogen peroxide, buffered sodium peroxyborate, or peroxycarbonate), cetyl pyridinium chloride, magnolia extract, magnolol, honokiol, 5,5'-dibutyl-2,2'-diol, propyl honokiol, borinic acid esters, and mixtures thereof. Anti-attachment agents such as Solrol also can be included, as well as plaque dispersing agents such as enzymes (papain, glucoamylase, etc.).

The present inventors have discovered that the use of the chalcone compounds of the invention, in combination with antimicrobial agents, can significantly enhance the efficacy of the antimicrobial agent. Enhancing the efficacy can result in the use of lower concentrations of antimicrobial agents to achieve the same or similar effect achieved when the antimicrobial agents were used alone. The amount of antimicrobial agent can be reduced by anywhere from 10% to more than 50% of its concentration when used alone, without the chalcone compound of the invention, preferably, from 10% to 75%, more preferably from about 10% to about 50%.

In an embodiment, as set forth in detail elsewhere herein, the combination of both a chalcone compound, preferably 3-(4'-Hydroxy-3'-methoxy-phenyl)-1-phenyl-prop-2-ene-1-one, and an antimicrobial agent provides a synergistic effect on the inhibition of biofilm formation and/or biofilm degradation. The present inventors found a surprising reduction in Biofilm Eradication Concentration ($BEC_{50}$), which is the lowest concentration at which greater than 50% reduction in biomass is observed relative to control. The $BEC_{50}$ of the chalcone compound and antimicrobial agents is lower when they are tested together for biofilm inhibition compared to when they are tested separately.

Accordingly, in a preferred embodiment the chalcone compound has a $BEC_{50}$ in the presence of the antimicrobial agent of 50% or less, more preferably 30% or less, most preferably 25% or less, compared to the $BEC_{50}$ of chalcone compound not in the presence of the antimicrobial agent. The chalcone compound preferably has a $BEC_{50}$ in the presence of the antimicrobial agent of 0.1 ppm to 40 ppm, more preferably 0.2 ppm to 30 ppm, more preferably 0.2 ppm to 30 ppm.

In a preferred embodiment the antimicrobial agent has a $BEC_{50}$ in the presence of the chalcone compound of 75% or less, more preferably 50% or less, compared to the $BEC_{50}$ of the antimicrobial agent alone (not in the presence of the chalcone compound. The $BEC_{50}$ of the antimicrobial agent in the presence of the chalcone compound depends upon the specific antimicrobial agent used in the composition. The antimicrobial agent may typically have a $BEC_{50}$ of 30 ppm or less in the presence of the chalcone compound. The antimicrobial agent preferably has a $BEC_{50}$ of 20 ppm or less, more preferably 6 ppm or less, most preferably 2 ppm or less in the presence of the chalcone compound. In one embodiment, wherein the antimicrobial agent is Triclosan, Triclosan has a $BEC_{50}$ of from 0.5 ppm to 3 ppm in the presence of the chalcone compound, more preferably a $BEC_{50}$ of 0.75 ppm to 1.5 ppm, whereas the $BEC_{50}$ of Triclosan alone is in the range of from about 1.5 to about 2.5 ppm.

In various embodiments of the present invention, where the carrier of the oral care composition is solid or a paste, the oral composition preferably comprises a dentally acceptable abrasive material, which serves to either polish the tooth enamel or provide a whitening effect. Non-limiting examples include silica abrasives such as silica gels and precipitated silicas. Commercial embodiments include ZEODENT® 115, marketed by J. M. Huber, Edison, N.J., United States of America, and SYLODENT® XWA, SYLODENT® 783 or SYLODENT® 650 XWA of the Davison Chemical Division of W. R. Grace & Co., New York, N.Y., United States of America, and SORBOSIL® silica abrasives, marketed by PQ Corporation, Malvern, Pa., United States of America. Other useful dentifrice abrasives include, without limitation, sodium metaphosphate, potassium metaphosphate, tricalcium phosphate, dihydrated dicalcium phosphate, aluminum silicate, calcined alumina, bentonite or other siliceous materials, or combinations thereof.

The abrasive is present in an effective amount. In embodiments where the oral composition is in a solid or paste form, the abrasive material is generally present at about 10% to about 99% of the oral composition. In certain embodiments, the polishing material is present in amounts ranging from about 10% to about 75% (for example about 10% to about 40% or about 15% to about 30%) in toothpaste, and from about 70% to about 99% in toothpowder.

In a still further embodiment a composition of the invention comprises at least one humectant, useful for example to prevent hardening of a toothpaste upon exposure to air. Any orally acceptable humectant can be used, including without limitation polyhydric alcohols such as glycerin, sorbitol, xylitol and low molecular weight PEGs. Most humectants also function as sweeteners. One or more humectants are optionally present in a total amount of about 1% to about 70%, for example about 1% to about 50%, about 2% to about 25%, or about 5% to about 15% by weight of the composition.

In a still further embodiment a composition of the invention comprises at least one surfactant, useful for example to compatibilize other components of the composition and thereby provide enhanced stability, to help in cleaning the dental surface through detergency, and to provide foam upon agitation, e.g., during brushing with a dentifrice composition of the invention. Any orally acceptable surfactant, most of which are anionic, nonionic or amphoteric, can be used. Suitable anionic surfactants include without limitation water-soluble salts of $C_{8-20}$ alkyl sulfates, sulfonated monoglycerides of $C_{8-20}$ fatty acids, sarcosinates, taurates, and the like. Illustrative examples of these and other classes include sodium lauryl sulfate, sodium coconut monoglyceride sulfonate, sodium lauryl sarcosinate, sodium lauryl isethionate, sodium laureth carboxylate and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation derivatives of $C_{8-20}$ aliphatic secondary and tertiary amines having an anionic group such as carboxylate, sulfate, sulfonate, phosphate or phosphonate. A suitable example is cocoamidopropyl betaine. One or more surfactants are optionally present in a total amount of about 0.01% to about 10%, for example about 0.05% to about 5% or about 0.1% to about 2% by weight of the composition.

In another embodiment, the composition comprises an orally acceptable anticalculus agent. One or more such agents can be present. Suitable anticalculus agents include without limitation phosphates and polyphosphates (for example pyrophosphates), polyaminopropanesulfonic acid (AMPS), zinc citrate trihydrate, polypeptides such as polyaspartic and polyglutamic acids, polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example the alkali metal and ammonium salts. Useful inorganic phosphate and polyphosphate salts illustratively include monobasic, dibasic and tribasic sodium phosphates, sodium tripolyphosphate (STPP), tetrapolyphosphate, mono-, di-, tri- and tetrasodium pyrophosphates, disodium dihydrogen pyrophosphate, sodium trimetaphosphate, sodium hexametaphosphate and the like, wherein sodium can optionally be replaced by potassium or ammonium. Other useful anticalculus agents include polycarboxylate polymers. These include polymers or copolymers of monomers that contain carboxylic acid groups, such as acrylic acid, methacrylic acid, and maleic acid or anhydride. Non-limiting examples include polyvinyl methyl ether/maleic anhydride (PVME/MA) copolymers, such as those available under the GANTREZ® brand from ISP, Wayne, N.J., United States of America. Still other useful anticalculus agents include sequestering agents including hydroxycarboxylic acids such as citric, fumaric, malic, glutaric and oxalic acids and salts thereof, and aminopolycarboxylic acids such as ethylenediaminetetraacetic acid (EDTA). One or more anticalculus agents are optionally present in the composition in an anticalculus effective total amount, typically about 0.01% to about 50%, for example about 0.05% to about 25% or about 0.1% to about 15% by weight.

In various embodiments, the anticalculus system comprises a mixture of sodium tripolyphsophate (STPP) and a tetrasodium pyrophosphate (TSPP). In various embodiments, the ratio of TSPP to STPP ranges from about 1:2 to about 1:4. In a preferred embodiment, the first anticalculus active ingredient, TSPP is present at about 1 to about 2.5% and the second anticalculus active ingredient, STPP is present at about 1 to about 10%.

In various embodiments, the anticalculus system further comprises a synthetic anionic polycarboxylate polymer. In one embodiment, the synthetic anionic polycarboxylate is present from about 0.1% to about 5%. In another embodiment, the synthetic anionic polycarboxylate is present from about 0.5% to about 1.5%, most preferably at about 1% of the oral care composition. In one embodiment according to the present invention, the anticalculus system comprises a copolymer of maleic anhydride and methyl vinyl ether, such as for example, the GANTREZ® S-97 product discussed above.

In various embodiments, the ratio of TSPP to STPP to the synthetic anionic polycarboxylate ranges from about 5:10:1 to about 5:20:10 (or 1:4:2). In one embodiment, the anticalculus system of the oral care composition comprises TSPP, STPP, and a polycarboxylate such as a copolymer of maleic anhydride and methyl vinyl ether at a ratio of about 1:7:1. In a non-limiting embodiment, the anticalculus system consists essentially of TSPP present at about 0.5% to about 2.5%, STPP present at about 1% to about 10%, and a copolymer of maleic anhydride and methyl vinyl ether present at about 0.5% to about 1.5%.

In a still further embodiment a composition of the invention comprises at least one thickening agent, useful for example, to impart a desired consistency and/or mouth feel to the composition. Any orally acceptable thickening agent can be used, including without limitation carbomers, also known as carboxyvinyl polymers, carrageenans, also known as Irish moss and more particularly ι-carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. One or more thickening agents are optionally present in a total amount of about 0.01% to about 15%, for example about 0.1% to about 10% or about 0.2% to about 5% by weight of the composition.

In a still further embodiment a composition of the invention comprises at least one viscosity modifier, useful for example, to inhibit settling or separation of ingredients or to promote redispersibility upon agitation of a liquid composition. Any orally acceptable viscosity modifier can be used, including without limitation mineral oil, petrolatum, clays and organo-modified clays, silica, and the like. One or more viscosity modifiers are optionally present in a total amount of about 0.01% to about 10%, for example about 0.1% to about 5% by weight of the composition.

In another embodiment, the composition comprises an orally acceptable source of fluoride ions. One or more such sources can be present. Suitable sources of fluoride ions include fluoride, monofluorophosphate and fluorosilicate salts, and amine fluorides, including olaflur (N'-octadecyltrimethylendiamine-N,N,N'-tris(2-ethanol)-dihydrofluoride). Any such salt that is orally acceptable can be used, including without limitation alkali metal (e.g., potassium, sodium), ammonium, stannous and indium salts, and the like. Water-soluble fluoride-releasing salts are typically used. One or more fluoride-releasing salts are optionally present in an amount providing a total of about 100 to about 20,000 ppm, about 200 to about 5,000 ppm, or about 500 to about 2,500 ppm, fluoride ions. Where sodium fluoride is the sole fluoride-releasing salt present, illustratively an amount of about 0.01% to about 5%, about 0.05% to about 1% or about 0.1% to about 0.5%, sodium fluoride by weight can be present in the composition.

Other components include, without limitation, flavorants, colorants, and other active ingredients such as antioxidants and anti-inflammation agents. The components are formulated into oral compositions according to known procedures.

Toothpastes and gels contain major amounts of humectants and usually an abrasive compound or compounds for teeth cleaning They are formulated with various active ingredients, such as anticaries agents, antiplaque compound, anti-inflammation agents, and the like, in addition to an antibacterial compound and an efflux pump inhibitor.

Mouth rinses and mouth washes contain the efflux pump inhibitors and antibacterial agents in a liquid carrier such as water or water/ethanol. Generally, the compositions contain a major amount of solvent, up to 98 or 99% by weight. The active compound (I) is optionally formulated together with surfactants, colorants, flavorants, and other active ingredients.

The orally acceptable vehicle or carrier in a lozenge bead or tablet is a non-cariogenic, solid water-soluble polyhydric alcohol (polyol) such as mannitol, xylitol, sorbitol, malitol, hydrogenated starch hydrozylate, hydrogenated glucose, hydrogenated disaccharides, hydrogenated polysaccharides, and the like in an amount of about 85% to about 95% of the total composition. Emulsifiers such as glycerin, and tableting lubricants, in minor amounts of about 0.1% to 5%, may be incorporated into the tablet, bead or lozenge formulation to facilitate the preparation of the tablet beads and lozenges. Suitable lubricants include vegetable oils such as coconut oil, magnesium stearate, aluminum stearate, talc, starch and Carbowax. Suitable non-cariogenic gums include kappa carrageenan, carboxymethyl cellulose, hydroxyethyl cellulose, and the like.

The lozenge, bead or tablet may optionally be coated with a coating material such as waxes, shellac, carboxymethyl cellulose, polyethylene/maleic anhydride copolymer or kappa-carrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet, bead and lozenge compositions of this embodiment affords a relatively longer time period of contact of the teeth in the oral cavity with the antibacterial and efflux pump inhibitor of the present invention.

Chewing gum formulations typically contain a chewing gum base, one or more plasticizing agents, at least one sweetening agent and at least one flavoring agent, in addition to antibacterial compound and efflux pump inhibitor compounds. It is preferably a sugarless gum.

Gum base materials are well known in the art and include natural or synthetic gum bases thereof. Representative natural gums or elastomers include chicle, natural rubber, jelutong, balata, guttapercha, lechi caspi, sorva, guttakay, crown gum, and perillo, or mixtures thereof. Representative synthetic gums or elastomers include butadiene-styrene copolymers, polyisobutylene and isobutylene-isoprene copolymers. The gum base is incorporated in the chewing gum product at a concentration of about 10% to about 40% and preferably about 20% to about 35%.

Plasticizing/softening agents include without limitation gelatin, waxes and mixtures thereof in amounts of about 0.1% to about 5%. The sweetening agent ingredient used in the practice of this invention may be selected from a wide range of materials, and include the same artificial and polyol sweeteners used for the preparation of tablets, beads and lozenges.

Polyol sweeteners such as sorbitol and malitol are present in the chewing gum composition of the present invention in amounts of about 40% to about 80% and preferably about 50% to about 75%. In a non-limiting embodiment, an artificial sweetener is present in the chewing gum composition of the present invention in amounts of about 0.1% to about 2% and preferably about 0.3% to about 1%.

The preferred embodiments now will be explained with reference to the following non-limiting examples.

Example 1

Preparation of 3-(4"-Hydroxy-3"-methoxy-phenyl)-1-(2'-hydroxy-5'-methoxy-phenyl)-prop-2-ene-1-one (CK-1)

2-hydroxy-5-methoxy acetophenone (10 gm, 0.06 mol) and 3-methoxy-4-hydroxy benzaldehyde (10 gm, 0.06 mol) were added to the solution of 6 gm of sodium hydroxide in 30 mL distilled water in a 250 mL round bottom flask at 0° C. Temperature of reaction was maintained below 15° C. with occasional shaking for 200 hr. Reaction mixture was neutralized with 5% aqueous HCl in ice cold conditions. Neutralised mixture was extracted with chloroform and purified by column chromatography using Silica gel to obtain 2, m.p. 121.5° C., $^1$HNMR: $\delta$ 3.84 (s, 3H), $\delta$ 3.97 (s, 3H), $\delta$6.96 (m, 2H), $\delta$ 7.14 (m, 2H), $\delta$ 7.24 (d, 1H), $\delta$ 7.39 (bs, 1H), $\delta$ 7.44 (d, 1H, J=15.31 Hz), $\delta$ 7.86 (d, 1H, J=15.31 Hz).

Example 2

Preparation of 3-(4'-Hydroxy-3'-methoxy-phenyl)-1-phenyl-prop-2-ene-1-one (CK-4)

3-methoxy-4-hydroxybenzaldehyde (20 gm, 0.132 mol) was added to the solution of acetophenone (20 gm, 0.125 mol) dissolved in acetic acid (20 mL) in a round bottom flask with constant stirring. Temperature of reaction was maintained below 15° C. with Occasional shaking for 200 hrs. Reaction mixture was poured in ice cold water and the product was extracted with chloroform. Chloroform extract was distilled under reduced pressure and the residue was chromatographed on SiO$_2$ gel to obtain 1. m.p. 91° C.

$^1$HNMR: $\delta$ 3.94 (s, 3H), $\delta$ 6.96 (d, 1H, J=8.11 Hz), $\delta$ 7.13 (d, 1H, J=1.78 Hz), $\delta$ 7.22 (dd, 1H, J=8.11 Hz and 1.78 Hz), $\delta$ 7.37 (d, 1H, J=15.30 Hz), $\delta$ 7.50 (m, 2H), $\delta$ 7.57 (m, 1H), $\delta$ 7.75 (d, 1H, J=15.30 Hz), $\delta$ 8.01 (m, 2H).

Example 3

Preparation of 3-(2",3"-Dimethoxy-phenyl)-1-furan-2-yl-prop-2-ene-1-one (CK-14)

2.3-dimethoxybenzaldehyde (4.69 gm, 0.018 mol) was added to the solution of 2-acetylfuran (2 gm, 0.018 mol) in methanol (10 ml) in a round bottom flask. To this solution 10% aqueous NaOH solution (4 ml) was added with stirring. Temperature of reaction was maintained below 15° C. and stirring was continued for 24 hrs. The reaction mixture was then poured in with vigorous stirring ice cold water and product was filtered. Recrystallization of product was done with ethanol. m.p. 109.8° C.

$^1$HNMR: $\delta$ 3.80 (s, 3H), $\delta$ 3.88 (s, 3H), $\delta$ 6.69 (dd, 1H, J=3.56 and 1.99 Hz), $\delta$ 7.00 (bs, 3H), $\delta$ 7.54 (bs, 1H), $\delta$ 7.60 (d, 1H, J=15.80 Hz), $\delta$ 7.84 (bs, 1H), 8.14 (d, 1H, J=15.80 Hz).

Example 4

Preparation of 3-(2",5"-dimethoxy-phenyl)-1-(1H-pyrrol-2-yl)-prop-2-ene-1-one (CK-16)

2.5-dimethoxybenzaldehyde (0.76 gm, 0.004 mol) was added to the solution of 2-acetylpyrrole (0.5 gm, 0.004 mol) in methanol (10 ml) in a 100 ml Rb. To this solution 10% aqueous NaOH solution (2 ml) was added with stirring. Temperature of reaction was maintained below 15° C. and stirring was continued for 15 hrs. The reaction mixture was then poured in with vigorous stirring ice cold water and product was filtered. Recrystallization of product was done with ethyl acetate. m.p. 122.6° C.

$^1$HNMR: $\delta$3.86 (s, 6H), $\delta$6.35 (bs, 1H), $\delta$ 6.96 (d, 1H, J=6.35 Hz), $\delta$ 7.17 (m, 3H), $\delta$7.28 (bs, 1H), $\delta$ 7.42 (d, 1H, J=15.90 Hz), $\delta$ 8.11 (d, 1H, J=15.90 Hz).

Example 5

Decrease in the MIC of ciprofloxacin Against *Staphylococcus aureus* 1199B (NorA Overexpressing) when used in Combination with 3-(4'-Hydroxy-3'-methoxy-phenyl)-1-phenyl-prop-2-ene-1-one (CK-4)

Minimum Inhibitory Concentration (MIC) of ciprofloxacin alone and in combination with the above mentioned chalcone compound was performed against *Staphylococcus aureus* 1199B, using method described in the study design. Up to sixteen-fold reduction in MIC of ciprofloxacin was observed in combination with chalcone compound at 50 µg/ml (Table 1).

TABLE 1

MICs of ciprofloxacin alone and in combination with 3-(4'-Hydroxy-3'-methoxy-phenyl)-1-phenyl-prop-2-ene-1-one (CK-4) against *Staphylococcus aureus* 1199B (Nor A overexpressing)

| (CK-4) Conc (µg/ml) | MIC (µg/ml) of ciprofloxacin for *Staphylococcus aureus* 1199B |
|---|---|
| — | 8.0 |
| 6.25 | 4.0 |
| 12.5 | 2.0 |
| 25.0 | 1.0 |
| 50.0 | 0.5 |

Example 6

Decrease in the MIC of tetracycline Against *Staphylococcus aureus* SA-K2192 (TetK Overexpressing) when used in Combination with 3-(4'-Hydroxy-3'-methoxy-phenyl)-1-phenyl-prop-2-ene-1-one (CK-4)

Minimum Inhibitory Concentration (MIC) of tetracycline alone and in combination with the above mentioned chalcone compound was performed against *Staphylococcus aureus* SA-K2192, using method described in the study design. Up to eight-fold reduction in MIC of tetracycline was observed in combination with chalcone compound at 50 µg/ml (Table 2).

TABLE 2

MICs of tetracycline alone and in combination with 3-(4'-Hydroxy-3'-methoxy-phenyl)-1-phenyl-prop-2-ene-1-one (CK-4) against *Staphylococcus aureus* SA-K2192 (TetK overexpressing)

| (CK-4) Conc (µg/ml) | MIC (µg/ml) of tetracycline for *Staphylococcus aureus* SA-K2192 |
|---|---|
| — | 32 |
| 6.25 | 32 |
| 12.5 | 16 |
| 25.0 | 8.0 |
| 50.0 | 4.0 |

Example 7

**Decrease in the MIC of tetracycline Against *Staphylococcus aureus* SA-K2191 (MsrA Overexpressing) when used in Combination with 3-(4'-Hydroxy-3'-methoxy-phenyl)-1-phenyl-prop-2-ene-1-one (CK-4)**

Minimum Inhibitory Concentration (MIC) of erythromycin alone and in combination with the above mentioned chalcone compound was performed against *Staphylococcus aureus* SA-K2191, using method described in the study design. Up to eight-fold reduction in MIC of erythromycin was observed in combination with chalcone compound at 50 µg/ml (Table 3).

TABLE 3

MICs of erythromycin alone and in combination with 3-(4'-Hydroxy-3'-methoxy-phenyl)-1-phenyl-prop-2-ene-1-one (CK-4) against *Staphylococcus aureus* SA-K2191 (MsrA overexpressing)

| (CK-4) Conc (µg/ml) | MIC (µg/ml) of erythromycin for *Staphylococcus aureus* SA-K2191 |
|---|---|
| — | 64 |
| 6.25 | 64 |
| 12.5 | 32 |
| 25.0 | 16 |
| 50.0 | 8.0 |

Example 8

**Decrease in the MIC of ciprofloxacin Against *Staphylococcus aureus* 1199B (NorA Overexpressing) when used in Combination with 3-(2",3"-Dimethoxy-phenyl)-1-furan-2-yl-prop-2-ene-1-one (CK-14)**

Minimum Inhibitory Concentration (MIC) of ciprofloxacin alone and in combination with the above mentioned chalcone compound was performed against *Staphylococcus aureus* 1199B, using method described in the study design. Up to eight-fold reduction in MIC of ciprofloxacin was observed in combination with chalcone compound at 50 µg/ml (Table 4).

TABLE 4

MICs of ciprofloxacin alone and in combination with 3-(2",3"-Dimethoxy-phenyl)-1-furan-2-yl-prop-2-ene-1-one (CK-14) against *Staphylococcus aureus* 1199B (Nor A overexpressing)

| (CK-4) Conc (µg/ml) | MIC (µg/ml) of ciprofloxacin for *Staphylococcus aureus* 1199B |
|---|---|
| — | 8.0 |
| 6.25 | 8.0 |
| 12.5 | 4.0 |
| 25.0 | 2.0 |
| 50.0 | 1.0 |

Example 9

**Decrease in the MIC of tetracycline Against *Staphylococcus aureus* SA-K2192 (TetK Overexpressing) when used in Combination with 3-(2",3"-Dimethoxy-phenyl)-1-furan-2-yl-prop-2-ene-1-one (CK-14)**

Minimum Inhibitory Concentration (MIC) of tetracycline alone and in combination with the above mentioned chalcone compound was performed against *Staphylococcus aureus* SA-K2192, using method described in the study design. Up to four-fold reduction in MIC of tetracycline was observed in combination with chalcone compound at 50 µg/ml (Table 5).

TABLE 5

MICs of tetracycline alone and in combination with 3-(2",3"-Dimethoxy-phenyl)-1-furan-2-yl-prop-2-ene-1-one (CK-14) against *Staphylococcus aureus* SA-K2192 (TetK overexpressing)

| (CK-4) Conc (µg/ml) | MIC (µg/ml) of tetracycline for *Staphylococcus aureus* SA-K2192 |
|---|---|
| — | 32 |
| 6.25 | 32 |
| 12.5 | 16 |
| 25.0 | 16 |
| 50.0 | 8.0 |

Example 10

**Decrease in the MIC of tetracycline Against *Staphylococcus aureus* SA-K2191 (MsrA Overexpressing) when used in Combination with 3-(2",3"-Dimethoxy-phenyl)-1-furan-2-yl-prop-2-ene-1-one (CK-14)**

Minimum Inhibitory Concentration (MIC) of erythromycin alone and in combination with the above mentioned chalcone compound was performed against *Staphylococcus aureus* SA-K2191, using method described in the study design. Up to four-fold reduction in MIC of erythromycin was observed in combination with chalcone compound at 50 µg/ml (Table 6).

TABLE 6

MICs of erythromycin alone and in combination with
3-(2'',3''-Dimethoxy-phenyl)-1-furan-2-yl-prop-
2-ene-1-one (CK-14) against *Staphylococcus aureus*
SA-K2191 (MsrA overexpressing)

| (CK-4) Conc (µg/ml) | MIC (µg/ml) of erythromycin for *Staphylococcus aureus* SA-K2191 |
|---|---|
| — | 64 |
| 6.25 | 64 |
| 12.5 | 32 |
| 25.0 | 32 |
| 50.0 | 16 |

Example 11

Potentiation of Activity of Triclosan Against *Streptococcus mutans, Actinomyces viscosus* and *Fusobacterium nucleatum* when used in Combination with 3-(4'-Hydroxy-3'-methoxy-phenyl)-1-phenyl-prop-2-ene-1-one (CK-4)

Minimum Inhibitory Concentration (MIC) of triclosan alone and in combination with the above mentioned chalcone compound was performed against *Streptococcus mutans, Actinomyces viscosus* and *Fusobacterium nucleatum*, using method described in the study design. Four to eight-fold reduction in MIC of triclosan was observed in combination with chalcone compound (Table 7).

TABLE 7

MICs of triclosan alone and in combination with 3-
(4'-Hydroxy-3'-methoxy-phenyl)-1-phenyl-prop-
2-ene-1-one (CK-4) against *Streptococcus mutans,
Actinomyces viscosus* and *Fusobacterium nucleatum*.

| | MIC (µg/ml) of Triclosan | | | |
|---|---|---|---|---|
| | | With CK-4 (µg/ml) | | |
| Organisms | Alone | 6.25 | 12.5 | 25 |
| S. mutans | 4.0 | 2.0 | 1.0 | 0.5 |
| A. viscosus | 4.0 | 2.0 | 1.0 | 0.5 |
| F. nucleatum | 2.0 | 1.0 | 1.0 | 0.5 |

Example 12

Potentiation of Activity of magnolol Against *Streptococcus mutans, Actinomyces viscosus* and *Fusobacterium nucleatum* when used in Combination with 3-(4'-Hydroxy-3'-methoxy-phenyl)-1-phenyl-prop-2-ene-1-one (CK-4)

Minimum Inhibitory Concentration (MIC) of magnolol alone and in combination with the above mentioned chalcone compound was performed against *Streptococcus mutans, Actinomyces viscosus* and *Fusobacterium nucleatum*, using method described in the study design. Up to sixteen-fold reduction in MIC of magnolol was observed in combination with chalcone compound (Table 8).

TABLE 8

MICs of magnolol alone and in combination with 3-(4'-Hydroxy-
3'-methoxy-phenyl)-1-phenyl-prop-2-ene-1-one (CK-4) against
*Streptococcus mutans, Actinomyces viscosus* and
*Fusobacterium nucleatum*.

| | MIC (µg/ml) of Magnolol | | | |
|---|---|---|---|---|
| | | With CK-4 (µg/ml) | | |
| Organisms | Alone | 6.25 | 12.5 | 25 |
| S. mutans | 4.0 | 2.0 | 1.0 | 0.5 |
| A. viscosus | 4.0 | 1.0 | 0.5 | 0.25 |
| F. nucleatum | 2.0 | 1.0 | 1.0 | 0.5 |

Example 13

Potentiation of Activity of 5,5'-dibutylbiphenyl-2,2'-diol Against *Streptococcus mutans, Actinomyces viscosus* and *Fusobacterium nucleatum* when used in Combination with 3-(4'-hydroxy-3'-methoxy-phenyl)-1-phenyl-prop-2-ene-1-one (CK-4)

Minimum Inhibitory Concentration (MIC) of 5,5'-dibutylbiphenyl-2,2'-diol alone and in combination with the above mentioned chalcone compound was performed against *Streptococcus mutans, Actinomyces viscosus* and *Fusobacterium nucleatum*, using method described in the study design. Two to four-fold reduction in MIC of 5,5'-dibutylbiphenyl-2,2'-diol was observed in combination with chalcone compound (Table 9).

TABLE 9

MICs of 5,5'-dibutylbiphenyl-2,2'-diol alone and
in combination with 3-(4'-Hydroxy-3'-methoxy-phenyl)-
1-phenyl-prop-2-ene-1-one (CK-4) against *Streptococcus mutans,
Actinomyces viscosus* and *Fusobacterium nucleatum*.

| | MIC (µg/ml) of Butyl magnolol | | | |
|---|---|---|---|---|
| | | With CK-4 (µg/ml) | | |
| Organisms | Alone | 6.25 | 12.5 | 25 |
| S. mutans | 4.0 | 4.0 | 2.0 | 1.0 |
| A. viscosus | 4.0 | 4.0 | 2.0 | 1.0 |
| F. nucleatum | 2.0 | 2.0 | 2.0 | 1.0 |

Example 14

Potentiation of Activity of Honokiol against *Streptococcus mutans, Actinomyces viscosus* and *Fusobacterium nucleatum* when used in Combination with 3-(4'-Hydroxy-3'-methoxy-phenyl)-1-phenyl-prop-2-ene-1-one (CK-4)

Minimum Inhibitory Concentration (MIC) of honokiol alone and in combination with the above mentioned chalcone compound was performed against *Streptococcus mutans, Actinomyces viscosus* and *Fusobacterium nucleatum*, using method described in the study design. Four to eight-fold reduction in MIC of honokiol was observed in combination with chalcone compound (Table 10).

TABLE 10

MICs of honokiol alone and in combination with 3-(4'-Hydroxy-3'-methoxy-phenyl)-1-phenyl-prop-2-ene-1-one (CK-4) against *Streptococcus mutans, Actinomyces viscosus* and *Fusobacterium nucleatum*.

| | MIC (µg/ml) of Honokiol | | | |
|---|---|---|---|---|
| | | With CK-4 (µg/ml) | | |
| Organisms | Alone | 6.25 | 12.5 | 25 |
| S. mutans | 4.0 | 2.0 | 1.0 | 0.5 |
| A. viscosus | 4.0 | 2.0 | 1.0 | 0.5 |
| F. nucleatum | 2.0 | 1.0 | 1.0 | 0.5 |

Example 15

Reduction in the Dose Requirement of Ciprofloxacin when used in Combination with 3-(4'-Hydroxy-3'-methoxy-phenyl)-1-phenyl-prop-2-ene-1-one (CK-4) in Systemic Infection Model of Mice The study was conducted to see the in vivo response of ciprofloxacin in combination with the above-mentioned efflux pump inhibitor. The Swiss albino mice were infected intravenously with *Staphylococcus aureus* ATCC 29213 ($10^7$ CFU/mouse). The infected mice were divided in groups and each group consisted of 6 mice. The treatment consisted of one dose immediately after the infection followed by the next dose after a gap of 6 hrs. The result was recorded as number of survivals each day. The mice were observed for seven days and $ED_{50}$ was determined after seven days of observation. The $ED_{50}$ for ciprofloxacin was 9.2 mg/kg and in combination with the CK-4 the $ED_{50}$ for ciprofloxacin was reduced to 5.86 mg/kg.

Example 16

Reduction in Biofilm Eradication Concentration ($BEC_{50}$) for Antibacterial Agents when used in Combination with 3-(4'-Hydroxy-3'-methoxy-phenyl)-1-phenyl-prop-2-ene-1-one (CK-4)

The compound CK-4 was first tested to assess whether it had antimicrobial efficacy on its own. An MIC assay was performed on two known anti-bacterial agents, as well as CK-4, using *A. viscosus* as the reference organism. The results are shown in Table 11 below:

TABLE 11

| Compound | MIC (*A. viscosus*) |
|---|---|
| CK-4 | >100 ppm |
| Triclosan | 3.5 ppm |
| CPC | <1 ppm |

From the above table, it is clear to see that CK-4 has considerably higher MIC than two commonly used antibacterial agents (triclosan and cetyl pyridinium chloride (CPC)). This indicates that CK-4 alone is not a strong antibacterial agent and will, at the levels used in formulations, contribute very little to the overall antibacterial efficacy.

*Actinomyces viscosus* (ATCC#43146) was grown in trypticase soy broth supplemented with 0.6% yeast extract (TSB-YE) at 37° C., static culture. For mixed species assays, the source of bacteria was a continuous culture chemostat inoculated with *A. viscosus, Lactobacillus casei* (ATCC #334), *Streptococcus oxalis* (ATCC #35037), *Fusobacterium nucleatum* (ATCC #10953), and *Veilonella parvula* (ATCC #17745). This mixed culture was maintained in a specialized complex medium in a continuous culture chemostat at 37° C.

MIC assays were performed using *A. viscosus* as a reference organism. Compounds to be tested were plated in the duplicate rows of the first column of a sterile 96-well culture plate. Two-fold serial dilutions were performed into 0.5×TSB across the plate. *A. viscosus* bacteria were grown over night in TSB-YE at 37° C., static culture. Overnight cultures of bacteria were diluted to an $OD_{610}$~0.4 in 0.5×TSB. An equivalent volume of bacteria to the test solution was added to each well of the 96-well plate. Plates were incubated overnight at 37° C. to allow bacterial growth to occur. The $OD_{610}$ of the entire plate was read on a Perkin Elmer EnVision microplate reader. Absorbance values for duplicate wells were averaged and compared to values for wells containing bacteria in media alone. MIC values were determined as the concentration of active in the last well for which growth of bacteria was inhibited relative to the media controls. All plates contained two rows of Triclosan as a positive control.

To assess the bioenhancing ability of CK-4, inhibition of single species biofilm formation tests were conducted. Actives of interest were plated in the first column of a sterile 384-well culture plate and serial twofold dilutions were performed across the plate in 0.5× TSB. First generation cultures of *A. Viscosus* bacteria were grown overnight in TSB-YE. Cultures were diluted to an $OD_{610}$~0.2 in 0.5×TSB and plated in the wells containing serial dilutions of actives. Plates were incubated for 24 hours at 37° C. to allow growth and biofilm formation to occur.

Following incubation, supernatants were removed from the plate and remaining biofilms were stained with 0.03% Grain's crystal violet. Stained plates were read on a Perkin Elmer EnVision microplate reader for absorbance at 590 nm. Absorbances were compared to the absorbance of wells treated with media alone and results are reported as a percent reduction in biofilm formation relative to media control. The $BEC_{50}$ is defined as the lowest concentration at which greater than 50% reduction in biofilm density (as read by the absorbance of the dye used to stain the biofilm) relative to a media only control. A compound with a lower $BEC_{50}$ is considered to be more efficacious than one with a higher level. The results are shown in Table 12 below for a variety of known antibacterial agents.

TABLE 12

$BEC_{50}$ of antibacterial agents alone, and with CK-4

| Antibacterial | $BEC_{50}$ alone | $BEC_{50}$ with CK-4 |
|---|---|---|
| Zinc Citrate | 41.67 | 20.83 |
| Triclosan | 1.95 | 0.98 |
| THC | 31.25 | 26.04 |
| Catechin | 26.04 | 26.04 |
| CPC | 1.95 | 0.49 |
| *Magnolia* | 3.91 | 1.95 |
| Magnolol | 3.91 | 1.95 |
| Honokiol | 5.21 | 2.60 |
| Butyl Magnolol | 0.65 | 0.24 |
| Propyl Honokiol | 0.49 | 0.65 |

The results of this experiment reveal that the addition of CK-4 has the potential to dramatically and unexpectedly increase the efficacy of several antimicrobial compounds, despite not having any strong antibacterial activity of its own. The effect was particularly strong for cetyl pyridinium chloride (CPC), which resulted in nearly a 4-fold decrease in $BEC_{50}$, when compared to CPC alone, thus enabling the use of much lower concentrations of antimicrobial to achieve the same antibacterial efficacy (up to 75% less CPC, when used together with CK-4).

We claim:

1. A composition comprising a carrier and as active ingredients
    an antimicrobial agent selected from zinc citrate, triclosan, tetrahydrocannabinol, cetyl pyridinium chloride, magnolia, magnolol, honokiol and butyl magnolol, and
    one chalcone compound selected from the group consisting of 3-(4'-Hydroxy-3'-methoxy-phenyl)-1-(2'hydroxy-5' methoxy-phenyl)-prop-2-ene-1-one, 3-(4'-Hydroxy-3'-methoxy-phenyl)-1phenyl-prop-2-ene-1-one, 3-(2",3"-Dimethoxy-phenyl)-1-furan-2-yl-prop-2-ene-1-one, 3-(2",5"-dimethoxy-phenyl)-1-(1H-pyrrol-2-yl)-prop-2-ene-1-one, and mixtures thereof.

2. The composition according to claim 1, is an oral care composition, optionally wherein the oral care composition is in the form of a dentifrice selected from the group consisting of toothpaste, tooth powder, gel, rinse, lozenge, chewing gum, film, and mixtures thereof.

3. The composition of claim 1, wherein the chalcone compound is 3-(4'-Hydroxy-3'-2-methoxy-phenyl)-1-phenyl-prop-2-ene-1-one.

4. A composition as claimed in claim 1 wherein the active ingredients are present in an effective concentration for treating a microbial infection by topical administration to the oral cavity of a mammal in need thereof.

5. A composition according to claim 4 wherein the microbial infection is caused by a bacterium.

6. A composition as claimed in claim 5, wherein the composition is in the form of a dentifrice selected from the group consisting of toothpaste, tooth powder, gel, rinse, lozenge, chewing gum, film, and mixtures thereof.

7. A composition as claimed in claim 4, wherein the chalcone compound is 3-(4'-Hydroxy-3'-methoxyphenyl)-1-phenyl-prop-2-ene-1-one.

8. A composition as claimed in claim 4 wherein the microbial count is reduced.

9. The composition of claim 1 wherein the antimicrobial agent is zinc citrate.

10. The composition of claim 9 wherein the chalcone compound is 3-(4'-hydroxy-3'-methoxyphenyl)-1-phenyl-prop-2-ene-1-one.

* * * * *